US008343495B2

(12) United States Patent
Brock

(10) Patent No.: US 8,343,495 B2
(45) Date of Patent: Jan. 1, 2013

(54) **EQUINE ANTIBODIES AGAINST *BACILLUS ANTHRACIS* FOR PASSIVE IMMUNIZATION AND TREATMENT**

(75) Inventor: Kenny V. Brock, Notasulga, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/685,302

(22) Filed: Jan. 11, 2010

(65) Prior Publication Data

US 2010/0239595 A1    Sep. 23, 2010

Related U.S. Application Data

(60) Provisional application No. 61/204,753, filed on Jan. 10, 2009.

(51) Int. Cl.
*A61K 39/395* (2006.01)
(52) U.S. Cl. .................. 424/164.1; 424/246.1
(58) Field of Classification Search .......... None
See application file for complete search history.

(56) References Cited

U.S. PATENT DOCUMENTS

| | | | |
|---|---|---|---|
| 4,911,910 A | 3/1990 | Mifflin | |
| 6,913,756 B1 * | 7/2005 | Kearney | 424/246.1 |
| 7,442,373 B2 | 10/2008 | Morrow et al. | |
| 7,601,351 B1 | 10/2009 | Rosen et al. | |
| 2002/0082386 A1 * | 6/2002 | Mangold et al. | 530/350 |
| 2003/0118591 A1 * | 6/2003 | Levy | 424/165.1 |
| 2004/0009182 A1 | 1/2004 | Myers et al. | |
| 2004/0258699 A1 * | 12/2004 | Bowdish et al. | 424/184.1 |
| 2005/0112145 A1 * | 5/2005 | Hudson et al. | 424/235.1 |
| 2005/0271689 A1 * | 12/2005 | Huang et al. | 424/246.1 |
| 2006/0258842 A1 * | 11/2006 | Groen et al. | 530/350 |
| 2007/0231334 A1 * | 10/2007 | Alibek et al. | 424/164.1 |
| 2009/0098164 A1 * | 4/2009 | Bhatt et al. | 424/246.1 |
| 2010/0062415 A1 * | 3/2010 | Schwoebel et al. | 435/5 |
| 2010/0255026 A1 * | 10/2010 | Stump et al. | 424/197.11 |

FOREIGN PATENT DOCUMENTS

WO    2008/115198    * 9/2008

OTHER PUBLICATIONS

Jones et al, Journal of Bacteriology, vol. 94 (3), Sep. 1967, pp. 609-614, Antibiotic treatment of Anthrax Infection in Mice.*
Kleine et al, Journal of Immunology, 1963, vol. 91, pp. 431-437.*
Lincoln, RE et al, Successful Treatment of Rhesus Monkeys for Septicemia anthrax, Antimicrobial Agents and Chemotherapy, 1964, vol. 10, pp. 759-763.*
Brachman, Philip S. et al, Vaccines, Chapter 31, Anthrax Vaccine pp. 887-903, 2004.*
Little, SF et al, Infection and Immunity, Comparative efficacy of *Bacillus anthracis* live spore vaccine and protective antigen vaccine against anthrax in the guinea pig.*
Fourth Edition, Anthrax in humans and Animals, World Health Organization, pp. 1-219, 2008.*

(Continued)

*Primary Examiner* — Albert Navarro
*Assistant Examiner* — Ginny Portner
(74) *Attorney, Agent, or Firm* — Andrus, Sceales, Starke & Sawall, LLP

(57) ABSTRACT

Disclosed are compositions and methods for treating a subject infected with *Bacillus anthracis* or at risk for infection with *B. anthracis*. The compositions include and the methods utilize isolated or purified equine antisera against *B. anthracis*.

11 Claims, 2 Drawing Sheets

OTHER PUBLICATIONS

Gold, H, Sep.-Oct. 1967, Treatment of Anthrax, Federation Proceedings, vol. 26(5), pp. 1563-1568.*

Feige, K et al, The Veterinary Journal, vol. 169, 2005, pp. 102-107, The effects of automated plasmapheresis on clinical, haematological, biochemical and coagulation variable in horses.*

Cohen, S. et al, Infection and Immunity, Attenuated Nontoxinogenic and Nonencapsulated Recombinant *Bacillus anthracis* spore vaccines protect against Anthrax, 2000, vol. 68(8), pp. 4549-4558.*

Thorne, Curtis B. et al, Journal of Bacteriology, 1960, vol. 79(3), p. 450-455, Production of toxin in vitro by *Bacillus anthracis* and its separation into two components.*

Pittman, Phillip R et al, Protective Antigen and Toxin neutralization antibody patterns in Anthrax vaccinees undergoing serial plasmapheresis, Clinical and Diagnostic Laboratory Immunology, Jun. 2005, pp. 713-721, vol. 12(6).*

Barnard, John P. et al, Infection and Immunity, vol. 67(2), pp. 562-567, col. 67(2), Feb. 1999, Vaccination against Anthrax with attenuated recombinant strains of *Bacillus anthracis* that produce Protective antigen.*

Bhatnagar et al., "Anthrax Toxin", Critical Reviews in Microbiology, 2001, 27(3):167-200.

Hering et al., "Validation of the anthrax lethal toxin neutralization assay", Biologicals, Mar. 2004, 32(1):17-27.

Lyons et al., "Murine Model of Pulmonary Anthrax: Kinetics of Dissemination, Histopathy, and Mouse Strain Susceptibility", Infection and Immunity, Aug. 2004, 72(8): 4801-4809.

Quinn et al., "Specific, Sensitive, and Quantitative Enzyme-Linked Immunosorbent Assay for Human Immunoglobulin G Antibodies to Anthrax Toxin Protective Antigen", Emerging Infectious Diseases, Oct. 2002, 8(10):1103-1110.

Phipps et al., "Rabbit and Nonhuman Primate Models of Toxin-Targeting Human Anthrax Vaccines", Microbiology and Molecular Biology Reviews, Dec. 2004, 68(4):617-529.

* cited by examiner

EQUINE ANTIBODIES AGAINST *BACILLUS ANTHRACIS* FOR PASSIVE IMMUNIZATION AND TREATMENT

CROSS-REFERENCE TO RELATED APPLICATIONS

The present application claims the benefit under 35 U.S.C. §119(e) to U.S. Provisional Patent Application No. 61/204,753, filed on Jan. 10, 2009, the content of which is incorporated herein by reference in its entirety.

BACKGROUND

The field of the invention relates to *Bacillus anthracis* and methods for passive immunization against infection by *Bacillus anthracis* and treatment of infection by *Bacillus anthracis*.

*Bacillus anthracis* is a Gram-positive, aerobic, spore-forming bacterium that causes the disease "anthrax." There are three primary routes of infection including pulmonary (via inhalation), gastrointestinal (via ingestion), and cutaneous (via skin contact).

After infection, *B. anthracis* secretes a tri-partite exotoxin that includes lethal factor (LF), edema factor (EF), and protective antigen (PA). Protective antigen is synthesized as a precursor protein having an N-terminal amino acid signal sequence which is cleaved from the precursor. The processed PA then binds to a cell surface receptor, after which, PA undergoes further processing and is cleaved to release a 20 kDa fragment leaving a 63 kDa fragment bound to the cell surface. The cell surface bound 63 kDa fragment of PA multimerizes and exposes a binding site for LF and EF, which bind the PA multimer to form an exotoxin complex bound at the cell surface. This exotoxin complex then is internalized by the cell where it exerts its toxic effects. Therefore, disruption of any step in formation of the exotoxin complex may prevent the toxic effects of anthrax infection.

The threat of an anthrax outbreak, for example through bioterrorism, has increased. Although anthrax vaccines exist, their availability currently is limited. Further, these vaccines require a multiple-dose, primary vaccination schedule followed by a yearly booster. Adverse reactions at the local-injection site may deter recipients from obtaining further doses or boosters.

Treatments for anthrax infection also exist. Inhalation anthrax and gastrointestinal anthrax generally are susceptible to a spectrum of antibiotics. However, successful therapy typically requires that antibiotics be administered prior to onset of signs and symptoms of infection. Furthermore, excessive use of antibiotics selects for resistant strains of anthrax.

For these reasons, there is a critical need for alternative treatment and prevention methods for anthrax infection. Immunotherapy, optionally in conjunction with antibiotics, presents a potentially viable option for addressing the extremely high case fatality rates associated with systemic anthrax. In particular, antibodies against PA can inhibit or prevent the toxic effects of *B. anthracis* infection. (See, e.g., Bhatnagar et al., Critical Reviews in Microbiology 27:167-200 (2001), the content of which is incorporated by reference in its entirety). Therefore, passive immunotherapy methods that utilize compositions comprising antibodies against *B. anthracis*, in particular, antibodies against PA or the other exotoxins of *B. anthracis*, are desirable.

SUMMARY

Disclosed are compositions and methods for treating a subject infected with *Bacillus anthracis* or at risk for infection with *B. anthracis*. The compositions include and the methods utilize isolated or purified equine antisera against *B. anthracis*. In some embodiments, the disclosed compositions include and the methods utilize equine plasma that comprises antibodies against one or more proteins of *B. anthracis*, and preferably antibodies against one or more of *B. anthracis* protective antigen (PA), lethal factor (LF), and edema factor (EF). The presently disclosed compositions include pharmaceutical compositions.

The compositions typically comprise equine antisera against *B. anthracis* and the compositions may be administered to a subject infected with *B. anthracis* or at risk for infection with *B. anthracis*. In some embodiments, the disclosed methods comprise administering to the subject an effective amount of plasma from an equine for treating the subject, where the equine has been immunized or hyperimmunized with a non-encapsulated live *Bacillus anthracis* spore vaccine.

The presently disclosed methods typically include administering a composition comprising equine antisera against *B. anthracis* and the equine antisera preferably include equine anti-PA antibodies. In some embodiments, the methods further include administering one or more antimicrobial agents (e.g., an antibiotic such as penicillin or ciprofloxacin) to the subject, before, concurrently with, or after administering the effective amount of equine plasma. The presently disclosed compositions, accordingly, may include one or more antimicrobial agents.

In some embodiments of the methods, the subject is infected with a strain of *B. anthracis* that is resistant to one or more antimicrobial agents or the subject is at risk for infection with a strain of *B. anthracis* that is resistant to one or more antimicrobial agents. For example, the subject may be infected with a strain of *B. anthracis* that is resistant to penicillin or ciprofloxacin or the subject may be at risk for infection with a strain of *B. anthracis* that is resistant to penicillin or ciprofloxacin.

Also disclosed are methods for preparing the presently disclosed compositions. The methods may include methods for obtaining equine plasma comprising antibodies against *Bacillus anthracis*. For example, the methods may include administering a non-encapsulated live *Bacillus anthracis* spore vaccine to an equine and isolating plasma from the equine. Suitable methods for isolating plasma from the vaccinated equine include, but are not limited to, performing plasmapheresis (e.g., continuous flow plasmapheresis). In some embodiments, antibodies against *B. anthracis* may be further isolated or purified from the equine plasma thus obtained. For example, anti-PA antibodies (or antibodies against the other exotoxins of *B. anthracis*) may be further isolated or purified from the equine plasma thus obtained.

DETAILED DESCRIPTION

Figure 1:
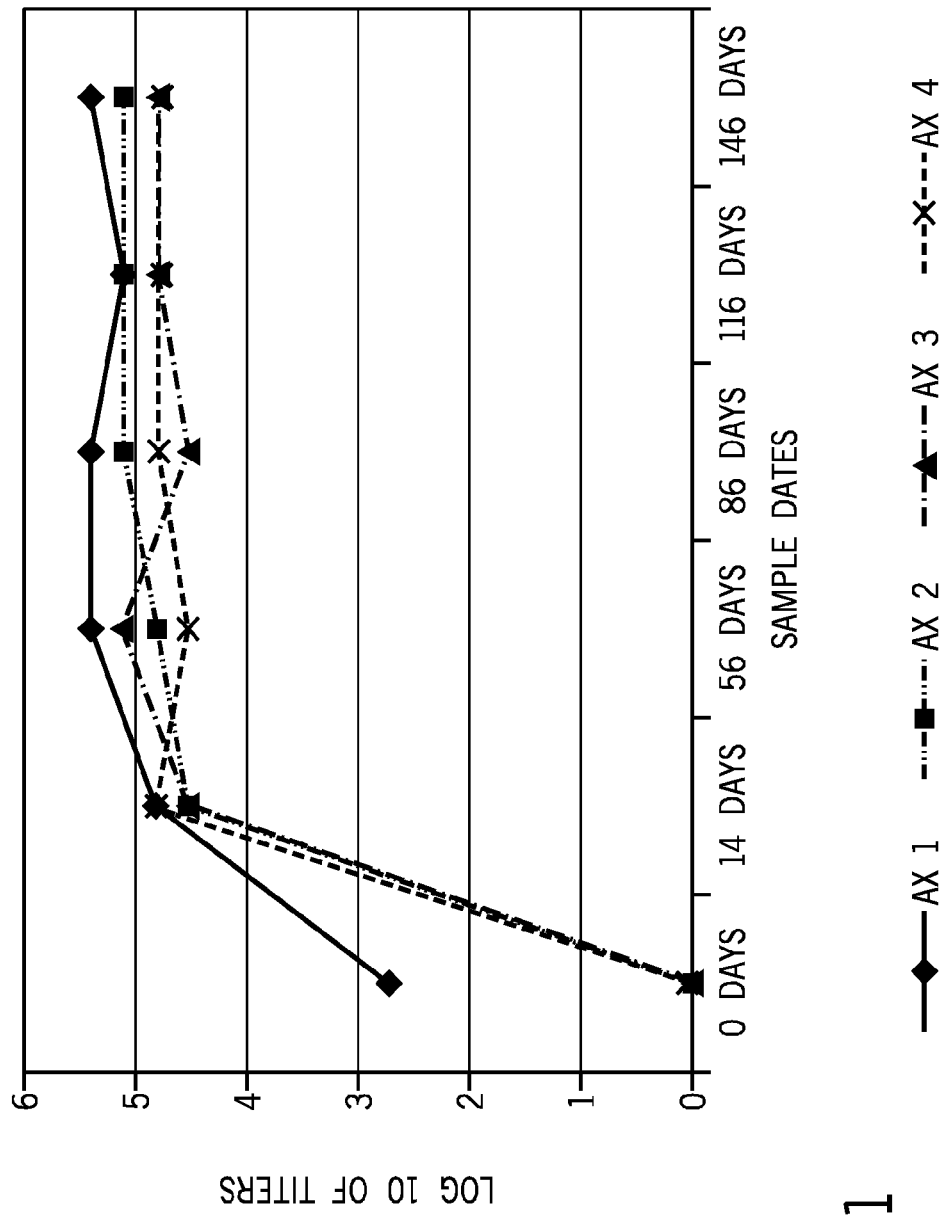
FIG. 1 illustrates the antibody titer response obtained from 4 horses that were immunized against anthrax over time. Equine hyperimmune plasma was produced by the repetitive immunization of horses using a commercially available live *Bacillus anthracis* spore vaccine (Colorado Serum Co.). The vaccine was administered in a 1.0 ml dose via two different routes, intramuscular and subcutaneously. Hyperimmunization was achieved by multiple monthly immunizations.

The present invention is described herein using several definitions, as set forth below and throughout the application.

Unless otherwise specified, the terms "a" or "an" mean "one or more."

As used herein, "about" and "substantially" will be understood by persons of ordinary skill in the art and will vary to some extent on the context in which they are used. If there are uses of the term which are not clear to persons of ordinary skill in the art given the context in which it is used, "about" will mean up to plus or minus 10% of the particular term and "substantially" will mean more than plus or minus 10% of the particular term.

As used herein, the terms "include" and "including" have the same meaning as the terms "comprise" and "comprising."

A "subject," "patient," "individual," or "host" refers to a human or non-human having, or at risk for acquiring an infection by B. anthracis. The terms "subject," "patient," "individual," or "host" may be used interchangeably.

The presently disclosed compositions typically include equine antibodies against B. anthracis. The compositions may include equine plasma or antisera which include equine polyclonal antibodies against B. anthracis. However, as used herein, the terms "antibody" and "antibodies" may refer not only to polyclonal antibodies, but also in some aspects to monoclonal antibodies, bi-specific antibodies, multispecific antibodies, grafted antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2, IgG3, IgG4, IgA1 and IgA 2) or subclass. The terms "antibody" and "immunoglobulin" may be used interchangeably herein.

As used herein, the term "plasma" means the liquid component of blood (i.e., whole blood minus blood cells) in which blood cells would normally be suspended. The term "serum" means plasma without fibrinogen or the other clotting factors (i.e., whole blood minus blood cells and the clotting factors). The term "antisera" means blood serum that contains antibodies that bind to a specific antigen (e.g., sera that includes anti-PA antibodies). The term "plasmapheresis" means a process that involves removal of blood from a donor, extraction of plasma from the removed blood, and reintegration of the removed blood after the plasma has been extracted.

The presently disclosed compositions may include equine plasma from an equine that has been immunized with one or more B. anthracis antigens. As used herein, the term "antigen" refers to a substance that is capable of inducing the production of an antibody or a T-cell response. Suitable antigens for the vaccines utilized herein for generating equine antisera may include, but are not limited to, PA, LF, and EF. Antigens for generating antibodies against PA are disclosed in U.S. Pat. Nos. 7,601,351 and 7,442,373, the contents of which are incorporated herein by reference in their entireties. Preferably, the equine plasma includes antibodies against PA (and optionally LF or EF). Accordingly, the equine may be immunized with a vaccine that includes PA, (or LF or EF) as an antigen, with a vaccine that includes live B. anthracis that expresses PA (or LF or EF), with a vaccine that includes nucleic acid that encodes PA (or LF or EF), or with a vaccine that includes a heterologous vector that expresses PA (or LF or EF).

During infection, Bacillus anthracis PA is synthesized as a 764 amino acid precursor (SEQ ID NO:1) which includes a 19 amino acid N-terminal signal sequence that is cleaved from the precursor. The processed precursor then binds to its cell surface receptor and undergoes further processing and is cleaved at the sequence RKKR (SEQ ID NO:2, residues 193-196) to release a 20 kDa N-terminal fragment leaving a 63 kDa C-terminal fragment bound to the cell surface. An exemplary amino acid sequence for B. anthracis PA is deposited at GenBank under accession no. AAA22637.1, which deposit information is incorporated herein by reference in its entirety.

The presently disclosed compositions preferably include equine antibodies that bind specifically to PA. In some embodiments, the compositions may include equine antibodies that bind specifically to antigenic PA polypeptides comprising SEQ ID NO:1 or a fragment (e.g., an epitope-bearing fragment), a derivative, a variant, an analog, or a modified form thereof. Suitable fragments, derivatives, variants, analogs, and modified forms of PA are described in U.S. Pat. No. 7,601,351, the content of which is incorporated herein by reference in its entirety. For example, the compositions may include equine antibodies that bind to a polypeptide having an amino acid sequence comprising one or more amino acid substitutions, deletions, or additions relative to SEQ ID NO:1.

As contemplated herein, equine plasma comprising antibodies against B. anthracis antigens may be obtained by immunizing an equine with a non-encapsulated live B. anthracis vaccine. For example, the equine may be administered live non-encapsulated Sterne Strain 34F2 spores in saponin (Anthrax Spore Vaccine, Colorado Serum Company, Denver, Colo.). The vaccine typically is administered intramuscularly or subcutaneously at a dosage of 1 ml. Other suitable vaccines may include, but are not limited to, inactivated B. anthracis vaccine, a polypeptide vaccine comprising one or more of the PA, LF, and EF polypeptide (e.g., a vaccine comprising the PA 764 aa precursor, the signal sequence processed PA 745 aa fragment, the PA 20 kDa fragment, the PA 63 kDa fragment, or another immunogenic fragment, derivative, variant, analog, or modified form thereof, such as a polypeptide having at least about 95% sequence identity to SEQ ID NO:1), a nucleic acid vaccine encoding one or more of the PA, LF, and EF polypeptide (e.g., a DNA vaccine encoding the PA 764 aa precursor, the signal sequence processed PA 745 aa fragment, the PA 20 kDa fragment, the PA 63 kDa fragment, or another immunogenic fragment, derivative, variant, analog, or modified form thereof, such as a polypeptide having at least about 95% sequence identity to SEQ ID NO:1), or a vector vaccine expressing one or more of the PA, LF, and EF polypeptide (e.g., a vector vaccine expressing the PA 764 aa precursor, the signal sequence processed PA 745 aa fragment, the PA 20 kDa fragment, the PA 63 kDa fragment, or another immunogenic fragment, derivative, variant, analog, or modified form thereof, such as a polypeptide having at least about 95% sequence identity to SEQ ID NO:1).

The presently disclosed compositions may be used to treat a subject infected with B. anthracis, for example by passive immunization. As used herein, the terms "treat," "treating" or "treatment," and other grammatical equivalents as used herein, include alleviating, inhibiting or reducing symptoms of the infection, reducing or inhibiting severity of the infection, reducing incidence of the infection, prophylactic treatment of the infection, reducing or inhibiting recurrence of the infection, preventing the infection, delaying onset of the infection, delaying recurrence of the infection, abating or ameliorating the infection or symptoms thereof, inhibiting the infection or symptoms thereof, e.g., arresting the development of the infection or symptoms thereof, relieving the symptoms of the infection, causing regression of the infection or the symptoms thereof, or stopping the symptoms of the infection. The terms further include achieving a therapeutic benefit. By therapeutic benefit is meant eradication or amelioration of the infection of symptoms thereof such that an improvement is observed in the individual.

The presently disclosed compositions may be used to prevent infection by B. anthracis in a subject, for example by passive immunization. As used herein, the terms "prevent," "preventing" or "prevention," and other grammatical equivalents as used herein, include preventing infection or the symptoms thereof, inhibiting the infection or symptoms thereof, e.g., arresting the development of the infection or symptoms thereof are intended to include prophylaxis. The terms further include achieving a prophylactic benefit. For prophylactic benefit, the compositions are optionally administered to an individual having or at risk of developing the infection or symptoms thereof.

The presently disclosed compositions typically include equine antibodies against B. anthracis as a therapeutic agent and further may include one or more additional therapeutic agents (i.e., a co-therapeutic agent). For example, additional therapeutic agents may include antimicrobial agents. Suitable antimicrobial agents may include, but are not limited to, penicillin, ciprofloxacin, doxycycline, amoxicillin, ampicillin, levofloxacin, gatifloxacin, and chloramphenicol. The presently disclosed compositions may include pharmaceutical combinations.

The present methods may include administration of equine antibodies as a first therapeutic agent and co-administration of a second therapeutic agent (i.e., a co-therapeutic agent) which may include antimicrobial agents. As used herein, the terms "co-administration", "administered in combination with" and their grammatical equivalents are meant to encompass administration of the selected therapeutic agents to a single individual, and are intended to include treatment regimens in which the agents are administered by the same or different route of administration or at the same or different times. For example, in some methods, antibodies against B. anthracis may be administered first to a subject, and subsequently antimicrobial agents may be administered to the subject. In other methods, antimicrobial agents may be administered first to the subject, and subsequently antibodies against B. anthracis may be administered to the subject. In further methods, antibodies against B. anthracis and antimicrobial agents may be administered at the same time to the subject, either in separate pharmaceutical compositions or in a single pharmaceutical composition (i.e., a pharmaceutical combination).

As used herein, the terms "effective amount" or "therapeutically effective amount," refer to a sufficient amount of at least one agent being administered which achieves a desired result, e.g., to prevent an infection or to relieve to some extent one or more symptoms of an infection. In certain instances, the result of administering an effective amount or a therapeutically effective amount is prevention of infection or reduction and/or alleviation of the signs, symptoms, or causes of the infection.

As used herein, the terms "administer," "administering", "administration," and the like, refer to the methods that are used to enable delivery of compositions or agents to the desired site of biological action. These methods include, but are not limited to parenteral injection, including infusion, intravenous, subcutaneous, intraperitoneal, intramuscular, or intravascular routes (e.g., for administration of antibodies against B. anthracis). Other methods include, but are not limited to oral routes, intraduodenal routes, topical and rectal administration (e.g., for administration of antimicrobial agents). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa., the content of which is incorporated herein by reference in its entirety.

The present compositions further may include one or more pharmaceutically acceptable carriers, diluents, or excipients. As used herein, the term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material is administered to an individual without causing significant undesirable biological effects or significantly interacting in a deleterious manner with any of the components of the composition in which it is contained.

The presently disclosed methods include methods of passively immunizing a subject against B. anthracis via administering equine antibodies against B. anthracis, for example as present in isolated horse plasma. Passive immunization, as used herein, shall be given its ordinary meaning and shall also mean the introduction of antibodies, for example, from a subject with active immunity (e.g., equine polyclonal antisera), or of genetically-engineered or synthetic antibodies, to treat infection. Passive immunization also shall include the administration of one or more antibodies, or fragments thereof, to confer immunity to a specific pathogen or toxin. Methods of passive immunization against B. anthracis are disclosed in U.S. Pat. Nos. 7,601,351 and 7,442,373 and U.S. Publication No. 20040009182, the contents of which are incorporated herein by reference in their entireties.

The presently disclosed compositions may be administered by any suitable route, preferably via infusion or intravenous injection. Formulations for infusion or injection optionally may be prepared in unit dosage form (e.g., in bags, ampoules, or single or multi-dose containers), and optionally may include an added preservative.

The presently disclosed methods may include administering a pharmaceutical composition comprising equine antibodies against B. anthracis to a subject having or at risk for acquiring an infection by B. anthracis that is resistant to one or more antimicrobial agents. In some embodiments, the subject has or is at risk for acquiring an infection by B. anthracis that is resistant to one or more antimicrobial agents selected from a group consisting of penicillin, ciprofloxacin, doxycycline, amoxicillin, ampicillin, levofloxacin, gatifloxacin, and chloramphenicol.

Hyperimmunization. The equine may be administered one or more doses of a suitable B. anthracis vaccine (e.g., non-encapsulated live B. anthracis spore vaccine, Colorado Serum Co., Denver, Co.). Preferably, the equine is administered a first dose, and subsequently is administered a second, third, fourth, or further dose, after waiting 2-3 weeks between doses. The equine may be administered a suitable B. anthracis vaccine in order to hyperimmunize the equine. For example, the equine may be administered a first dose. Then, approximately three weeks later, the equine may be administered a second dose. Then approximately three or four weeks later, the equine may be administered a third dose.

Hyperimmunization may be achieved by utilizing an accelerated immunization schedule, for example, via serial intradermal administration of a previously administered vaccine preparation approximately every 30 days. Following immunization and isolation of equine plasma, antibody levels to PA and the toxin neutralizing activity in the equine plasma to determine the optimal immunization regimen and plasmapheresis schedule. Hyperimmune status may be confirmed by collection of serum plasma 7-10 days following the final dose of the live anthrax vaccine (e.g., after administering a third or fourth dose).

Adjuvants. If needed, additional adjuvant may be included to optimize antibody response. The term "adjuvant" refers to a compound or mixture that enhances the immune response to an antigen. An adjuvant can serve as a tissue depot that slowly releases the antigen and also as a lymphoid system activator that non-specifically enhances the immune response. Examples of adjuvants which may be employed include Freund's adjuvant (complete Freund's adjuvant or incomplete Freund's adjuvant). Other suitable adjuvants may include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, nonionic block co-polymer adjuvants (e.g., CRL1005), aluminum phosphates (e.g., $AlPO_4$), R-848 (a Th1-like adjuvant), imiquimod, PAM3CYS, poly (I:C), loxoribine, potentially useful human adjuvants such as BCG (bacille Calmette-Guerin) and *Corynebacterium parvum*, CpG oligodeoxynucleotides (ODN), cholera toxin derived antigens (e.g., CTA1-DD), lipopolysaccharide adjuvants, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

Antibody Assay. Blood may be collected from the hyperimmunized equine and plasma may be isolated or purified from the blood. The titer of the plasma may be determined by a suitable antibody assay (e.g., the titer against PA or another exotoxin or protein of *B. anthracis* may be determined via an indirect linked immunosorbent assay (ELISA)). Two-fold serial dilutions of serum may be placed in 96-well plates coated with recombinant PA. After applying appropriate positive and negative control sera, plates may be incubated at 37° C. for 60 minutes and washed 3 times to remove unbound antibody. A peroxidase-conjugated goat anti-equine IgG antibody and peroxidase substrate may be added to detect bound antigen colorimetrically by measuring the optical density of the peroxidase-converted substrate. Titers may be determined by observing the highest dilution that yields a mean OD value equal to or greater than the cutoff value for the assay. (See, e.g., Quinn et al., Emerg. Infect. Dis. 10:1103-1110 (2002), the content of which is incorporated herein by reference in its entirety). Alternatively, the *B. anthracis* lethal toxin neutralization activity of the equine plasma may be determined utilizing a colorimetric toxin neutralization assay. (See, e.g., Hering et al., Biologicals 32:17-27 (2004), the content of which is incorporated herein by reference in its entirety). The assay may be performed by incubating test plasma dilutions with recombinant PA and lethal factor (LF) on confluent monolayers of J774A.1 cells. Cell viability after exposure may be determined by adding thiazolyl blue (MTT) in 50% dimethyl formamide and measuring specific OD values at 570 nm.

Plasmapheresis. Plasmapheresis procedures may be utilized to collect hyperimmune plasma from donor horses. For example, approximately 17-18 liters of plasma may be collected approximately every 2 weeks from an individual donor horse. Suitable plasmapheresis devices include Fenwal Auto C plasmapheresis devices. A closed sterile collection system may be utilized in order to obtain high quality equine source plasma. Plasma may be produced at a standardized 6% sodium citrate ratio in 20 liter collection bags.

Processing and Storage. Immediately following plasmapheresis, the equine source plasma may be aliquoted into 1 liter bottles, weighed, and labeled. Next, the equine source plasma may be slant frozen in the processed 1 liter bottles at −35° C. until ready for use as a therapeutic or otherwise.

ILLUSTRATIVE EMBODIMENTS

The following list of embodiments is illustrative and is not intended to limit the scope of the claimed subject matter.

Embodiment 1

A pharmaceutical composition comprising isolated plasma from an equine that has been immunized with a non-encapsulated live *Bacillus anthracis* spore vaccine.

Embodiment 2

The composition of embodiment 1, wherein the plasma comprises antibodies that bind specifically to one or more proteins of *Bacillus anthracis*.

Embodiment 3

The composition of embodiment 1 or 2, wherein the plasma comprises antibodies that bind specifically to one or more of *Bacillus anthracis* protective antigen (PA), lethal factor (LF), and edema factor (EF) (optionally where the plasma comprises one or more of an anti-PA titer, an anti-LF titer, and an anti-EF titer of at least about $10^4$, $10^5$, or $10^6$).

Embodiment 4

The composition of any of embodiments 1-3, further comprising one or more antimicrobial agents.

Embodiment 5

The composition of embodiment 4, wherein the antimicrobial agent is selected from a group consisting of penicillin, ciprofloxacin, doxycycline, amoxicillin, ampicillin, levofloxacin, gatifloxacin, and chloramphenicol.

Embodiment 6

A method for treating a subject infected by *Bacillus anthracis* or at risk for infection with *Bacillus anthracis*, the method comprising administering to the subject an effective amount of any of the compositions of embodiments 1-5.

Embodiment 7

A method for treating a subject infected by *Bacillus anthracis* or at risk for infection with *Bacillus anthracis*, the method comprising administering to the subject an effective amount of isolated plasma from an equine for treating the subject, wherein the equine has been immunized with a non-encapsulated live *Bacillus anthracis* spore vaccine.

Embodiment 8

The method of embodiment 7, wherein the animal is a human.

Embodiment 9

The method of embodiment 7 or 8, wherein the equine plasma comprises antibodies that bind specifically to one or more proteins of *Bacillus anthracis*.

Embodiment 10

The method of any of embodiments 7-9, wherein the equine plasma comprises antibodies that bind specifically to one or more of *Bacillus anthracis* protective antigen (PA), lethal factor (LF), and edema factor (EF).

Embodiment 11

The method of any of embodiments 7-10, further comprising administering one or more antimicrobial agents to the subject, before, concurrently with, or after administering the effective amount of plasma.

Embodiment 12

The method of any of embodiments 7-11, wherein the subject is infected by a strain of *Bacillus anthracis* that is resistant to one or more antimicrobial agents or the subject is at risk for infection by a strain of *Bacillus anthracis* that is resistant to one or more antimicrobial agents.

Embodiment 13

The method of embodiment 12, wherein the antimicrobial agent is selected from a group consisting of penicillin, ciprofloxacin, doxycycline, amoxicillin, ampicillin, levofloxacin, gatifloxacin, and chloramphenicol.

Embodiment 14

A method for obtaining equine plasma comprising antibodies against *Bacillus anthracis*, the method comprising administering a non-encapsulated live *Bacillus anthracis* spore vaccine to the equine and isolating plasma from the equine.

Embodiment 15

The method of embodiment 14, wherein the plasma is isolated by performing plasmapheresis.

Embodiment 16

The method of embodiment 15, wherein the plasma is isolated by performing continuous flow plasmapheresis.

Embodiment 17

The method of any of embodiments 14-16, wherein the non-encapsulated live *Bacillus anthracis* spore vaccine is Sterne Strain 34F2 spores in saponin.

Embodiment 18

The method of any of embodiments 14-17, wherein the non-encapsulated live *Bacillus anthracis* spore vaccine is administered intramuscularly or subcutaneously.

EXAMPLES

The following examples are illustrative and are not intended to limit the scope of the claimed subject matter.

Production of Equine Hyperimmune Plasma

Equine hyperimmune plasma was produced by the repetitive immunization of horses using a commercially available live *Bacillus anthracis* spore vaccine (Colorado Serum Co.). The vaccine was administered in a 1.0 ml dose via two different routes, intramuscular and subcutaneously in the neck or hip region. Hyperimmunization was achieved by multiple monthly immunizations and repeated every 30 to 60 days to maintain a state of hyperimmunization.

Figure 2:
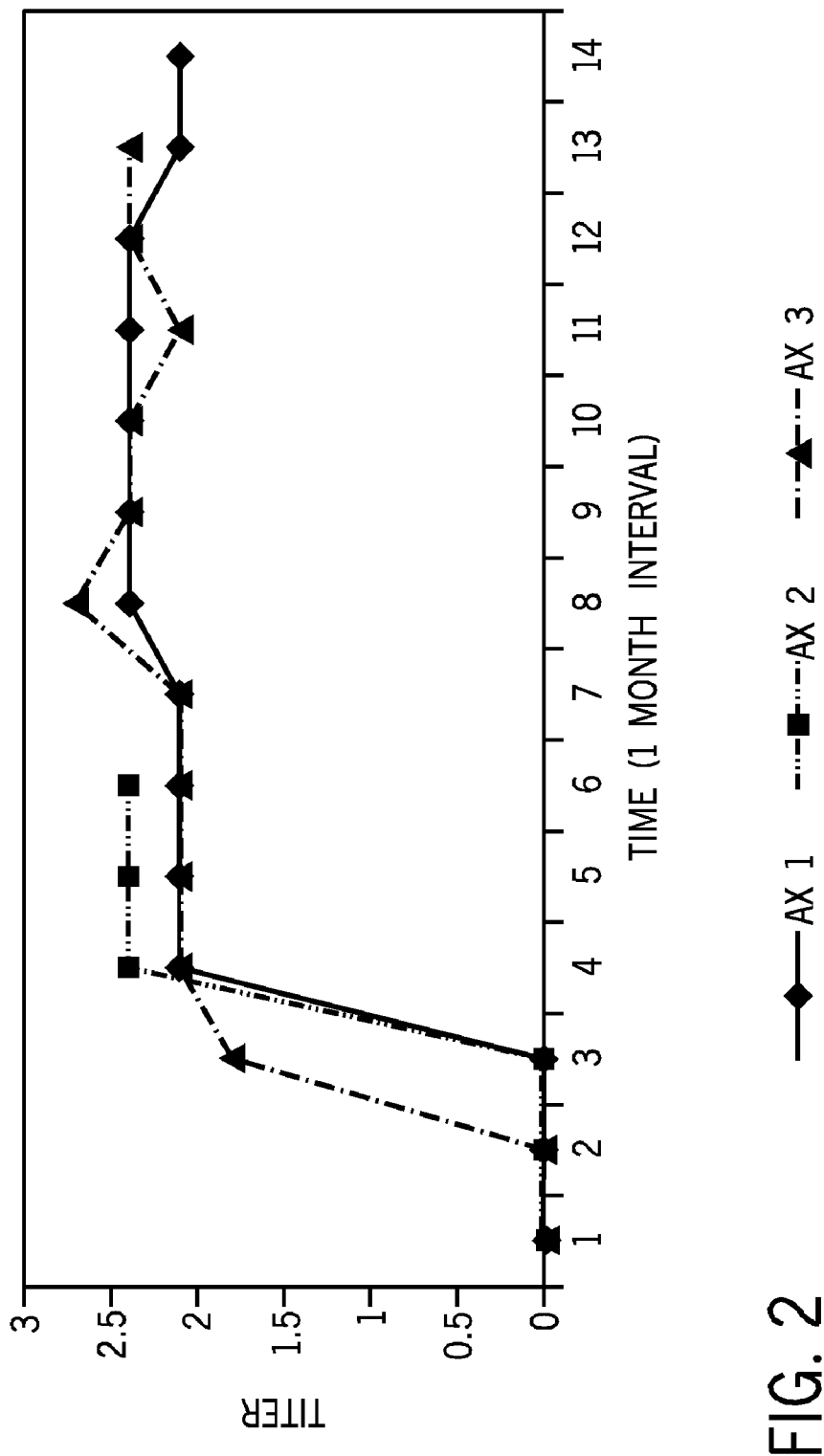
FIG. 2 illustrates the antibody titer response obtained from 3 horses of the 4 horses described for FIG. 1 that were immunized against anthrax over time.

The antiserum will be utilized as a polyclonal therapeutic against multiple antigens and/or virulence factors of *B. anthracis*, In vitro assays support the activity of the antiserum against *B. anthracis* protective antigen (PA) and lethal factor (LF), (see FIGS. 1 and 2).

The antibody titer response was determined in four (4) horses that were immunized against anthrax over time. Antibody titers were measured to the recombinant protective antigen (PA) of *Bacillus anthracis*. The assay was performed by ELISA. The titer data was graphed by taking the reciprocal log-10 of the titer dilution.

The antibody titer response further was determined in three (3) of the four (4) horses that were immunized against anthrax over time as described above. Antibody titers were measured by using an in vitro mouse macrophage neutralization assay utilizing purified *Bacillus anthracis* lethal factor. For neutralization assays, two-fold dilutions of horse plasma were prepared and protective antigen (1.0 g/ml) and lethal factor (0.5 g/ml) were added to the serum dilutions. Mouse macrophage cells (J774A.1) were added to a 96-well flat-bottomed tissue culture plate for 2 hours. The medium was removed and replace with 100 μl of the serum dilutions containing PA plus LF, and the plates were incubated for 4 hours at 37° C. in 5% $CO_2$. AlamarBlue was added at 10% of well volume, and the cells were incubuated for 20 h at 37° C. in 5% $CO_2$. Absorbance was measured at 590 nm (to detect oxidized AlamarBlue). The conversion of oxidized AlamarBlue to its reduced from was used to determine metabolic activity. Positive and negative controls were utilized. Receiprocal antibody titers were determined as the final dilution providing neutralization or inhibition of cytotoxity of PA/LF. Titer data was graphed by taking the reciprocal log-10 of the titer dilution.

In vivo activity of antisera collected from the immunized horses will be demonstrated using a mouse protection assay and a rabbit aerosol respiratory challenge assay. The mouse protection assay will be performed by intraperitioneal inoculation of the Ames strain of *Bacillus anthracis* into mice pretreated with serial dilutions of the antiserum preparations. This will provide reciprocal mouse neutralization assay titers indicative of protection. Other murine models of anthrax infection may be utilized. (See, e.g., Lyons et al., Infection and Immunity 72:4801-4809 (2004) (disclosing a murine model of pulmonary anthrax), the content of which is incorporated herein by reference in its entirety).

The utility of the antisera as a therapeutic against the respiratory form of anthrax will be demonstrated by using a rabbit aerosol respiratory challenge assay. This assay will be performed by an aerosol challenge of rabbits using the Ames strain of *B. anthracis*. Following the development of respiratory distress in the experimentally challenged rabbits, various doses will be used for intravenous treatment. Successful therapeutic dosing will be evident by resolution of the respiratory *B. anthracis* infection. Other rabbit and non-human primate models of anthrax infection may be utilized to assess the therapeutic value of the antisera. (See, e.g., Phipps et al., Microbiology and Molecular Biology Reviews 68:617-629 (2004), the content of which is incorporated herein by reference in its entirety).

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and methods described herein may be used alone or in combination with other compositions and methods. It is to be expected that various equivalents, alternatives and modifications are possible.

All publications and patent applications cited in this specification are herein incorporated by reference as if each individual publication or patent application were specifically and individually indicated to be incorporated by reference.

I claim:

1. A pharmaceutical composition comprising:
   (a) isolated plasma or sera from an equine that has been immunized with a non-encapsulated live *Bacillus anthracis* spore vaccine, wherein the plasma or sera has an anti-protective antigen (PA) titer of at least about $10^4$; and
   (b) one or more pharmaceutically acceptable carriers, diluents, or expients.

2. The composition of claim 1, wherein the plasma or sera has an anti-protective antigen (PA) titer of at least about $10^5$.

3. The composition of claim 1, further comprising one or more antimicrobial agents.

4. The composition of claim 3, wherein the antimicrobial agent is selected from a group consisting of penicillin, ciprofloxacin, doxycycline, amoxicillin, ampicillin, levofloxacin, gatifloxacin, and chloramphenicol.

5. Isolated equine plasma or sera comprising antibodies against *Bacillus anthracis* protective antigen (PA), wherein the titer of the antibodies is at least about $10^4$.

6. The isolated equine plasma or sera of claim 5, wherein the titer of the antibodies is at least about $10^5$.

7. A method for obtaining the isolated equine plasma or sera of claim 5, comprising administering a non-encapsulated live *Bacillus anthracis* spore vaccine to an equine and isolating plasma or sera from the equine.

8. The method of claim 7, wherein the plasma or sera is isolated by performing plasmapheresis.

9. The method of claim 8, wherein the plasma or sera is isolated by performing continuous flow plasmapheresis.

10. The method of claim 7, wherein the non-encapsulated live *Bacillus anthracis* spore vaccine is Sterne Strain 34F2 spores in saponin.

11. The method of claim 7, wherein the non-encapsulated live *Bacillus anthracis* spore vaccine is administered intramuscularly or subcutaneously.

* * * * *